United States Patent [19]

Gallegra et al.

[11] Patent Number: 5,637,775

[45] Date of Patent: Jun. 10, 1997

[54] PROCESS FOR THE PREPARATION OF HALOGENATED ETHERS

[75] Inventors: Pasquale Gallegra, Muttenz; Gerhard Degischer, Füllinsdorf, both of Switzerland

[73] Assignee: Saurefabrik Schweizerhall, Pratteln, Switzerland

[21] Appl. No.: 427,901

[22] Filed: Apr. 26, 1995

[30] Foreign Application Priority Data

Apr. 28, 1994 [CH] Switzerland .............. 1319/94
Nov. 1, 1994 [CH] Switzerland .............. 3265/94

[51] Int. Cl.$^6$ ............................................ C07C 27/04
[52] U.S. Cl. ............................................ 568/681
[58] Field of Search ............................................ 568/681

[56] References Cited

U.S. PATENT DOCUMENTS

| | | | |
|---|---|---|---|
| 2,527,376 | 10/1950 | Patrick | 260/79.1 |
| 3,883,602 | 5/1975 | Ens | 260/614 R |
| 3,972,947 | 8/1976 | Weinstock et al. | 260/614 R |
| 4,423,050 | 12/1983 | Verheyden et al. | 424/253 |
| 4,568,700 | 2/1986 | Warshowsky et al. | 521/31 |

FOREIGN PATENT DOCUMENTS 880 285  10/1952  Germany.
2 431 778  2/1975  Germany.

OTHER PUBLICATIONS

Topchii et al., Chemical Abstracts, vol. 89 (1978) Abstyract No. 129340c.
Kuraray Col, Chemical Abstracts, vol. 95 (1981) p. 600 Abstract No. 149932z corresponding JP81 65838 (English translation attached).
Fisser et al., Reagents for Organic Synthesis, vol. 7, J. Wiley & Sons, New York 1979 pp.228–229 and 299–300.
Corey et al., tetrahedron Letters, No. 11, pp. 809–812 (1976).

Wright et al., Macromolecules, 1991, vol. 24, pp. 5879–5880.

*Primary Examiner*—Paul J. Killos
*Assistant Examiner*—Dwayne C. Jones
*Attorney, Agent, or Firm*—Wenderoth, Lind & Ponack

[57] ABSTRACT

The invention relates to a process for the preparation of compounds of formula I

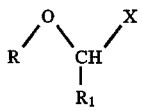

(I)

wherein

R is mono- or disubstituted lower alkyl, the substituents being selected from halogen and lower alkoxy, with the proviso that said substituents are not present at the carbon atom of the lower alkyl radical R linking the group R to the remainder of the molecule of formula I;

$R_1$ is hydrogen, lower alkyl, phenyl or phenyl-lower alkyl; and

X is chloro or bromo;

which comprises reacting an acetal of formula II,

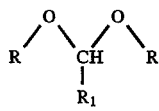

(II)

wherein

R and $R_1$ are as defined above,
with at least one compound of formula $R_2$—X, wherein $R_2$ is hydrogen or X—SO, in which last mentioned case the reaction mixture must contain a catalytically effective amount of N,N-di-lower alkyl-lower alkanoylamide(s) and wherein X is as defined with respect to the compounds of formula I. The compounds of formula I are useful intermediates, suitably for the synthesis of pharmaceutical or fungicidal compounds.

10 Claims, No Drawings

PROCESS FOR THE PREPARATION OF HALOGENATED ETHERS

BRIEF DESCRIPTION OF INVENTION

The present invention relates to a novel process for the preparation of 1-halogenated ethers which are used for the production of biologically active compounds, typically pharmaceuticals or fungicides.

The novel process for the preparation of compounds of formula I

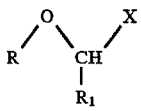

wherein

R is mono- or disubstituted lower alkyl, the substituents being selected from halogen and lower alkoxy, with the proviso that said substituents are not present at the carbon atom of the lower alkyl radical R linking the group R to the remainder of the molecule of formula I;

$R_1$ is hydrogen, lower alkyl, phenyl or phenyl-lower alkyl; and

X is chloro or bromo;

comprises reacting an acetal of formula II,

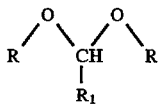

wherein

R and $R_1$ are as defined above, with at least one compound of formula $R_2$—X, wherein $R_2$ is hydrogen or X—SO, in which last mentioned case the reaction mixture must contain a catalytically effective amount of N,N-di-lower alkyl-lower alkanoylamide(s), and wherein X is as defined with respect to the compounds of formula I.

BACKGROUND OF INVENTION

It is known to prepare compounds of formula I by reacting the corresponding alcohols of formula $R_n$—OH, wherein $R_n$ typically has the meanings given for R in the definition of formula I, with formaldehyde or paraformaldehyde in the presence of an aqueous acid, e.g. of the corresponding hydrohalic acid (HBr or HCl) (q.v. Olah, G. A., et al., "Haloalkylations", in: Friedel-Crafts and Related Reactions, Vol. II, J. Wiley & Sons, New York, 1964, pp. 659–671 and 734–737; and U.S. Pat. No. 4,568,700, published Feb. 4, 1986). The drawback of the known processes is that (especially if R in $R_n$—OH is a secondary hydrocarbon radical, but also if R is a primary hydrocarbon radical) a substantial number of largely unwanted by-products are formed which result in a loss of yield, including also in particular the carcinogenic, and hence chronically toxic, bis(1-halo-lower alk-1-yl) ethers, for example the bis (chloromethyl) ether (cf. Tou., J. C., et at., "Possible Formation of bis(chloromethyl) ether from the Reactions of Formaldehyde and Chloride Ion", Anal. Chem. 48(7), 958–63 (1976)), and/or hinder working up.

DETAILED DESCRIPTION OF INVENTION

The invention has for its object the provision of a novel, useful and economic process for the preparation of compounds of formula I, which process also avoids the drawbacks referred to above and, in particular, makes it possible to obtain high yields, a minor amount of unwanted, non-reusable and/or toxic by-products, in particular carcinogenic by-products, a very pure final product and/or a reaction course giving useful, reusable by-products, and/or which makes possible a simple working up of the final product.

This object is achieved by the process referred to above and described in detail hereinbelow.

Lower alkyl is typically $C_1$–$C_7$alkyl in straight-chain or branched-chain configuration, and is suitably methyl, ethyl, propyl, isopropyl, butyl, isobutyl, sec-butyl, or also pentyl, isopentyl, neopentyl, hexyl or heptyl.

Substituted lower alkyl is one of the radicals cited in connection with the definition of lower alkyl and which is substituted by one or two members selected from the group consisting of halogen such as fluoro, iodo or, preferably, chloro or bromo, and lower alkoxy, typically ethoxy or, preferably, methoxy. A preferred substituted lower alkyl radical is lower alkyl which is substituted by one or two members selected from the group consisting of chloro, bromo and lower alkoxy, such as methoxy, and is typically 1,3-dichloro- or 1,3-dibromo-2-propyl, 2-chloro- or 2-bromoethyl, or 2-methoxyethyl. The halogen and/or lower alkoxy substituents are not present at the linking carbon atom, i.e. at the carbon atom which links the group R in formula I to the oxygen atom attaching to the remainder of the molecule in formula I.

Unless otherwise indicated, the qualifying term "lower" used in the definition of radicals such as lower alkyl or lower alkoxy denotes that the radicals in question contain up to at most 7, preferably up to at most 4, carbon atoms inclusive.

$R_2$ is either hydrogen (in which case the compound $R_2$—X is the corresponding hydrogen chloride or hydrogen bromide), or X—SO (in which case the compound $R_2$—X is the corresponding thionyl chloride $SOCl_2$ or thionyl bromide $SOBr_2$). Preferably X is chloro and the compound of formula $R_2$—X is hydrogen chloride or thionyl chloride. The combination of a reaction initially with (typically a minor amount of) $R_2$—X, wherein $R_2$ is hydrogen and X is chloro or bromo, and subsequently with a compound of formula $R_2$—X, wherein $R_2$ is X—SO, where X is chloro or bromo, is also possible and can result in an enhanced yield.

The compounds of formula I are useful intermediates or precursors of protective groups in organic synthesis, in particular for the preparation of medicaments and/or fungicides. They react with amines, alcohols or carboxylic acids, with attendant introduction of the group

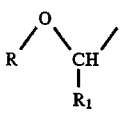

to the corresponding substituted amines, ethers and esters. The compounds of formula I are particularly suitable for the preparation of corresponding N-lower alkoxyalk-1-yl derivatives, e.g. N-[1-(1,3-dihydroxy-2-lower alkoxy)-lower alk-1-yl] derivatives of guaninane analogs, for example the compounds disclosed in EP 0 085 424 (published on 10th Aug., 1983), EP 0 187 297 (published on 12th Jul., 1986) and in EP 0 532 878 (published on 24th Mar., 1993), which have antiviral action. For example, 1,3-dichloro-2-chloromethoxypropane can be reacted with an alkali metal salt, e.g. the sodium salt, of propionic acid, to give 1,3-dipropionyloxy-2-propionyloxypropane (Example 2 in EP 0187 297), which can then be reacted to 9-(1,3-dihydroxy-2-propoxymethyl)guanine (=ganciclovir) in accordance with reaction scheme II in EP 0 187 297 by reaction with a protected guanine derivative and subsequent removal of the protective groups. The analogous preparation of e.g. 9-(2-hydroxyeth-1-oxymethyl)guanine (acyclovir) is possible. Specific compounds of formula I are also suitable for introducing protective groups in the course of syntheses, e.g. as hydroxyl protective groups. For example, 2-methoxyethoxymethyl chloride (1-chloromethoxy-2-methoxyethane)can be used for introducing the 2-methoxyethoxymethyl protective group (MEM group; q.v. Corey, E. J., et al., Tetrahedron Lett. 11,809–812 (1976)). This protective group is conveniently used in the preparation of 1,6,7,8,9,11a,12,13,14,14a-decahydro-1,13-dihydroxy-6-methyl-4H-cyclopent[f]oxacyclotridecin-4-one (Brefeldin A, i. a. fungicide) (q.v. M. Fieser and L. Fieser, Reagents for Organic Synthesis, Vol 7, S. 228–229, J. Wiley & Sons, New York/Chichester/Brisbane/Toronto 1979).

Specifically, the reaction proceeds as follows, and in the course of the reaction the following useful by-products may also be formed, depending on the reagent of formula $R_2$—X employed:

If $R_2$ is hydrogen, then the compound of formula $R_2$—X is a hydrogen chloride or hydrogen bromide of formula HX. The reaction runs essentially as follows:

Reaction scheme I:

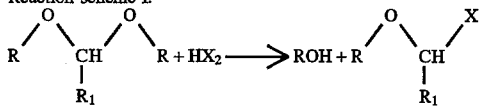

in which the substituents each have the meanings as given in connection with the definition of compounds of formula I, II and $R_2$—X. The resultant compound of formula ROH may be used to prepare once more the starting compound of formula II (q.v. below), so that in general high yields of compounds of formula I are possible.

The compound of formula I is obtained in surprisingly high purity. Unwanted by-products are formed only in unexpectedly low amount. In particular, very greatly reduced amounts of the corresponding toxic bis(1-halo-lower alk-1-yl) ethers are found, for example bis (chloromethyl) ether. Thus in Example 1 of this invention, the amount of bis(chloromethyl) ether is more than 200 times smaller than the amount obtained in prior art processes.

It is to be expressly emphasised that N,N-di-lower alkyl-lower alkanoylamides, such as N,N-dimethylformamide or N,N-dimethylacetamide, shall not be present in the reaction according to reaction scheme I.

If X is X—SO, then the compound of formula $R_2$—X is thionyl chloride or also thionyl bromide. The reaction proceeds essentially as follows:

Reaction scheme II:

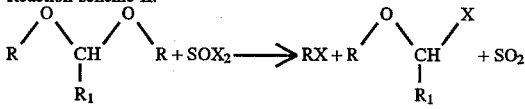

in which the substituents each have the meanings as given in connection with the definition of compounds of formula I, II and $R_2$—$X_n$. The radicals RX are brominated or chlorinated compounds which are themselves useful by-products (e.g. in the preparation of agrochemicals such as herbicides (q.v. DE-OS 33 03 388, published on 11th Aug., 1983, or U.S. Pat. No. 5,026,896, published on 25th Jun., 1991), of photographic bleach materials (q.v. DE-OS 26 51 969, published on 18th May, 1977), of dyes (q.v. EP 0 206 114, published on 30th Dec., 1986), or pharmaceuticals (e.g. antihypotensives etc., q.v. EP 0 111 455, published on 20th Jun., 1984), and hence contribute to the attractiveness of the reaction. This applies in particular to Cl—$CH_2$—$CH_2$—O—$CH_3$.

In this reaction too the compound of formula I is obtained in surprisingly high purity. Unwanted by-products are formed only in unexpectedly low amount. In particular, extremely small amounts of the corresponding toxic bis(1-halo-lower alk-1-yl) ethers are found, for example bis (chloromethyl) ether. Thus in Example 2 of this invention, the amount of bis(chloromethyl) ether is more than 100 times smaller than the amount obtained in prior art processes.

In addition, an unexpectedly simple working up is possible, for example by distillation, to obtain the final products of formula I in pure form.

To achieve the cited advantages in the reaction with $SOX_2$, it is necessary that catalytically effective amounts of one or more than one N,N-di-lower alkyl-lower alkanoylamide, preferably N,N-dimethylformamide or N,N-dimethylacetamide, shall be present in the reaction mixture, preferably in about a 0.0001- to 0.1-fold, preferably a 0.001- to 0.05-fold, molar ratio over the compound of formula II. The N,N-di-lower alkyl-lower alkanoylamide may also be used as solvent.

It is thus evident that the use of acetals of formula II for the preparation of α-chloro- and α-bromoalkyl ethers of formula I achieves surprisingly favourable results in the reaction with compounds of formula $R_2$—X.

The reaction in which $R_2$—X is hydrogen chloride or also hydrogen bromide, or that in which $R_2$—X is thionyl bromide or, preferably, thionyl chloride, is especially preferred. In this latter case, it can also be advantageous to add initially a small amount of $R_2$—X, wherein $R_2$ is hydrogen and X is chloro or bromo, and only then to carry out the reaction with thionyl bromide or thionyl chloride.

Unless otherwise specified, in the foregoing and subsequent description the substituents R, $R_1$, X and $R_2$ have the meanings given above in connection with the compounds of formula I, II and $R_2$—X.

The reactions of this invention preferably proceed using at least approximately equimolar amounts of the compound of formula $R_2$—X (based on the molar amount of the compound of formula II), in the presence of or, preferably, in the absence of solvents or diluents, conveniently at only slightly reduced to elevated temperature and with subsequent conventional working up of the reaction mixture.

The reaction can also be carried out in the presence of a Lewis acid as catalyst, provided $R_2$—X is hydrogen chloride or hydrogen bromide. It is preferred to carry out the reaction without a Lewis acid. As Lewis acid it is possible to use a catalytic amount, typically a c. 0.01-fold to c. 0.1-fold molar amount, for example the 0.02 to 0.05-fold molar amount (based on the molar amount of compound of formula II) of a halide or a metal of groups IIb, IIIb or IVb of the Periodic System of the Elements, e.g. appropriate zinc, tin, zirconium and aluminium halides.

It is advantageous to use a smaller, e.g. a 1.01- to 10-fold, molar excess, preferably a 1.01-to 8-fold molar excess, of the compound of formula $R_2$—X over the compound of formula II.

Suitable solvents are inert solvents such as aromatic hydrocarbons that may, however, only be used under the stated reaction conditions if they are inert, typically benzene or toluene, or halogenated aromatic hydrocarbons or haloalkanes such as di-, tri- or tetra-chloro-$C_1$-$C_4$alkanes, e.g. methylene chloride or trichlorethane, or chlorobenzene. The reaction of this invention may, however, be conveniently carried out without a solvent (in solution or in a melt), in which case the hydrohalic acid of formula $R_2$—X can be introduced in the gaseous state.

The reaction is expediently carried out in the range from slightly reduced to elevated temperature, the preferred range being from 0° C. to 150° C., typically from 10° to c. 120° C., most preferably from c. 15° to c. 115° C., depending on the reflux temperature which governs the upper limit, provided the reaction is not carried out under overpressure.

The reaction can be carried out under atmospheric pressure or under overpressure. The pressure may preferably be in the range from c. 0.5 to 250 bar, more particularly up to 50 bar, e.g. up to 10 bar.

Conventional working up is effected preferably by distillation, preferably under reduced pressure, e.g. from c. 0.1 to 200 mbar, typically from c. 10 to c. 30 mbar. In the reaction of reaction scheme I, the subsequent treatment of the alcohol ROH with thionyl chloride to give the corresponding chloro derivative RCl is also possible. This derivative is distilled from the reaction mixture, so that a back reaction is not possible and the reaction is thereby more complete. In principle, this variant is a combination of the reactions of reaction schemes I and II.

A preferred embodiment of the novel process comprises warming a mixture of an acetal of formula II to about 50°–70° C., introducing a c. 1.05- to 8-fold excess of the appropriate hydrogen chloride or hydrogen bromide ($R_2$—X) in gaseous form over about 2 to 10, preferably 4 to 6, hours; or adding dropwise a 1.01- to 3-fold excess of thionyl chloride or thionyl bromid (as $R_2$—X) over 1 to 5 hours at a temperature in the range from 10° to 115° C., allowing the reaction to proceed under stirring for further 0 to 5 hours; and then working up the resultant reaction mixture by distillation under reduced pressure, preferably from c. 10 mbar to to c. 30 mbar.

The invention relates to the preparation of compounds of formula I, wherein R is mono- or disubstituted lower alkyl, preferably $C_2$-$C_4$alkyl, typically ethyl, n-propyl, isopropyl, n-butyl, isobutyl or sec-butyl, the substituents being selected from halogen such as chloro or bromo, and lower alkoxy such as methoxy or ethoxy, with the proviso that said substituents are not present at the carbon atom of the lower alkyl radical R linking the group R to the remainder of the molecule of formula I; and wherein $R_1$ is hydrogen, lower alkyl, phenyl or phenyl-lower alkyl, preferably hydrogen or lower alkyl such as $C_1$-$C_4$alkyl; and wherein X is chloro or bromo, preferably chloro.

The invention preferably relates to the preparation of compounds of formula I, wherein R is lower alkyl of more than 2 carbon atoms, e.g. $C_2$-$C_4$alkyl, which is mono- or disubstituted by halogen such as chloro or bromo, or by $C_1$-$C_4$alkoxy such as methoxy, with the proviso that said substituents are not present at the carbon atom of the lower alkyl radical R linking the group R to the remainder of the molecule of formula I; preferably 1,3-dihalo-2-$C_3$-$C_7$alkyl, more particularly 1,3-dihalo-2-$C_3$-$C_4$alkyl, such as 1,3-dichloro- or 1,3-dibromo-2-propyl, or 2-($C_1$-$C_4$alkoxy) ethyl; wherein $R_1$ is hydrogen; and wherein X is chloro or bromo, preferably chloro; which comprises using the appropriately substituted starting materials.

The invention relates most preferably to the preparation of the compounds of formula I mentioned in the working Examples under the reaction conditions as generally defined hereinbefore or, in particular, under analogous process conditions to those set forth in the working Examples.

The starting compounds of formula II are known or they are prepared by per se known methods or they are commercially available.

The acetals of formula II are prepared by reacting the corresponding alcohols of formula III

R—OH (III)

wherein R has the given meanings, with appropriate aldehydes of formula IV

$R_1$—CHO (IV)

wherein $R_1$ has the given meanings, under process conditions which are known per se, conveniently by the methods described in "Houben-Weyl—Methoden der organischen Chemie", E. Müller et at. (Editor), Vol. 7, Part 1, 4th edition, Georg Thieme Verlag, Stuttgart, on p. 418 et seq., or in general accordance with the methods disclosed in U.S. Pat. No. 2,527,376 (published on 24th Oct., 1950). The compounds of formula IV can also be used as reactive precursors, e.g. paraformaldehyde ($R_1$=hydrogen).

The direct reaction of aldehydes of formula IV with the alcohols of formula III leads in the presence of hydrogen ions to the acetal of formula II via the step of the hemiacetal. In this reaction, water of reaction is preferably removed from the equilibrium, e.g. by distillation, or also by azeotropic distillation or by reaction with compounds such as orthosilicicates or dimethyl sulfite, with which the water of reaction combines immediately.

The hydrogen ions necessary for the reaction are preferably not generated by hydrohalic acids, or are generated only in the presence of very minor catalytic amounts thereof (to prevent the formation of toxic by-products); or primarily by addition of sulfuric acid or aliphatic or, preferably, aromatic sulfonic acids such as methanesulfonic acid, ethanesulfonic acid, benzenesulfonic acid, (lower alkylbenzene)sulfonic acid such as p-toluenesulfonic acid, or naphthalenesulfonic acid, most preferably p-toluenesulfonic acid, said aforementioned preferred acids being used in catalytic amount, typically in the c. 0.0001- 0.01-fold, preferably 0.001- to 0.01-fold, molar amount over the alcohol of formula III. The reaction is carried out preferably at elevated temperature, typically in the range from 30° to 150° C., preferably from c. 60° to c. 100° C., most preferably at c. 90° C.

The alcohol of formula III is preferably used in molar excess over the compound of formula IV in order to achieve as complete a reaction as possible to the acetal of formula II. The respective compound of formula III is preferably used in 1.5- to 10-fold excess, most preferably in 1.8- to 2.5-fold excess.

The reaction is carried out in the presence of or, preferably, in the absence of solvents, typically the solvents cited at the outset for the reaction of compounds of formula II with compounds of formula $R_2$—X.

If necessary, water formed during the reaction is removed by distillation (e.g. by azeotropic distillation). It is, however, also possible not to remove the water of reaction until after the reaction.

Working up is effected preferably by distillation of the reaction mixture, preferably under reduced pressure, conveniently at 0.1 to 100 mbar, the particularly preferred pressure range being from 1 to 30 mbar.

It is particularly preferred to react an alcohol of formula III as defined above, especially 1,3-dichloropropanol or 2-methoxyethanol, with an aldehyde of formula IV (or, in the case of the particularly preferred formaldehyde, a precursor thereof such as paraformaldehyde or trioxane), said alcohol of formula III being used in a 1,8- to 2,5-fold molar excess over the aldehyde of formula IV, in the temperature range from c. 60° to 120° C., in the presence of (based on the alcohol of formula III) a c. 0.001- to 0.01-fold molar amount of benzenesulfonic acid or, preferably, toluenesulfonic acid as catalyst, with subsequent removal of the water of reaction by distillation, followed by working up by distillation under reduced pressure, e.g. from c. 1 to c. 30 mbar.

A particularly preferred variant in the reaction with a compound of formula $SOX_2$, preferably with thionyl chloride, consists in a combination of the reaction of the alcohol of formula III and the aldehyde of formula IV, solely with removal of the water of reaction by distillation and of any unreacted starting material of formula III, but without subsequent isolation of the acetal of formula II in pure form (which would be possible by distillation of the reaction mixture, as described above), followed by direct reaction of the resultant reaction mixture with $SOX_2$ under the conditions already stated, especially with thionyl chloride (i.e. surprisingly also without removal of the acids employed that supply the hydrogen ions necessary for the reaction, conveniently the cited sulfonic acids, e.g. p-toluenesulfonic acid).

This variant means specifically in particular a process for the preparation of a compound of formula I, wherein R, $R_1$ and X are as defined above in connection with the compounds of formula I, which comprises reacting an alcohol of formula III,

R—OH  (III)

wherein R is as defined for compounds of formula I, with an appropriate aldehyde of formula IV $R_1$—CHO  (IV)

wherein $R_1$ is as defined for compounds of formula I, or a reactive derivative thereof, to give an acetal of formula II

wherein R and $R_1$ have the above meanings, solely (preferably at the conclusion of the reaction) with attendant removal of the water of reaction by distillation and of any unreacted starting material of formula III, but without subsequent isolation of the acetal of formula II in pure form, and thereafter further reacting the resultant reaction mixture direct with $X_2SO$, wherein X is as defined for compounds of formula I, with the proviso that a catalytically effective amount of N,N-di-lower alkyl-lower alkanoylamide(s) must be present.

This variant is therefore a reaction carried out in two steps consecutively in the same reactor (one-pot reaction). The additional advantages are that, in particular when using high-melting and high-boiling acetals of formula II, in particular bis[(2-chloro-1-chloromethyl)ethoxy]methane, the relatively troublesome purification (especially on an industrial scale) can be avoided, and the synthesis starting from the compounds of formulae III and IV can be carried out by a one-pot process. Yet only very minor amounts of toxic by-product, such as bis(chloromethyl) ether, are found (preferably less than 20 ppm in the final product of formula I which can be obtained by distillation, as described above). Particularly preferred is the process for the preparation of 1,3-dichloro-2-chloromethoxypropane of formula I, which comprises reacting formaldehyde or a reactive derivative thereof, preferably paraformaldehyde, with a molar excess (preferably a 1.5- to 10-fold excess) of 1,3-dichloropropan-2-ol in the presence of an aliphatic or aromatic sulfonic acid, preferably p-toluenesulfonic acid, in the presence of or, preferably, in the absence of solvents, at elevated temperature, preferably in the range from c. 60° to 100° C., to give his [(2-chloro-1-chloromethyl)ethoxy] methane of formula II, removing the water of reaction by distillation, if necessary distilling off unreacted 1,3-dichloropropan-2-ol (preferably under reduced pressure), and reacting the resulting mixture by adding a N,N-di-lower alkyl-lower alkanoylamide (preferably N,N-dimethylformamide), preferably in the 0.0001 to 0.1-fold molar excess over the bis[(2-chloro-1-chloromethyl)ethoxy]methane of formula II, and a compound of formula $R_2$—X, wherein $R_2$ is X—SO (preferably thionyl chloride), preferably in molar excess over the compound of formula II, more particularly in the 1.01- to 10-fold excess, which compound of formula $R_2$—X is conveniently added dropwise, in the temperature range from 0° to 150° C., preferably from 15° to 115° C., to give the final product which is obtained in pure form by working up, in particular by distillation. The individual process conditions may suitably conform to the particular conditions characterised above as being preferred.

If the educt is recycled, then yields of more than 97% can be readily achieved.

The invention also relates to the process comprising the entire reaction sequence starting from the alcohols of formula III and the aldehydes via the acetals of formula II and the reaction thereof with compounds of formula $R_2$—X, as defined above, to give the final products of formula I. Within the scope of this overall process, the process steps of the single steps cited as preferred and the starting materials substituted in conformity with the final products are likewise particularly preferred.

The invention is illustrated by the following Examples, but without in any way restricting the scope thereof. Temperatures are given in degrees Centigrade and pressures in mbar. $M_r$ denotes the relative molecular mass. 1,3-Dichloropropanol denotes 1,3-dichloropropan-2-ol.

EXAMPLE 1

Preparation of 1,3-dichloro-2-chloromethoxypropane 200 g of bis[(2-chloro-1-chloromethyl)ethoxy]methane ($M_r'$=269.9) are heated to c. 60° C. With stirring, a total amount of 100 g of hydrogen chloride ($M_r$=36.46) is then introduced over 5 hours. After 2 hours, the temperature is lowered to 15° C. The composition of the reaction mixture is determined in an aliquot of the mixture. The net result is as follows:

| resultant compound | amount |
| --- | --- |
| bis(2-chloro-1-chloromethyl)ethoxy-methane (educt) | 100 g |
| 1,3-dichloropropanol (by-product) | 47.7 g |
| 1,3-dichloro-2-chloromethoxypropane (product) | 65.5 g |
| bis(chloromethyl) ether (toxic by-product) | 20 mg |

The reaction proceeds essentially in accordance with the following formula:

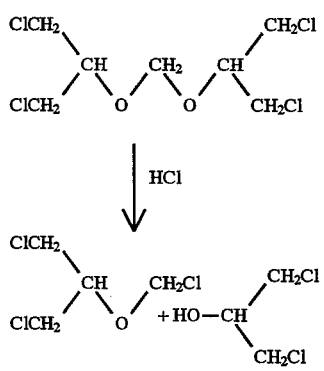

The reaction mixture is worked up by distillation under reduced pressure (c. 20 mbar), affording 1,3-dichloro-2-chloromethoxypropane ($M_r$=177.46) in 50% yield in more than 99% purity and containing less than 6 ppm of the toxic bis(chloromethyl) ether. 1,3-Dichloropropanol and bis(2-chloro-1-chloromethyl)ethoxymethane can be reused as starting material. Including the precursor cited below, this possibility of reusing the starting material makes it easy to obtain total yields of more than 95% over both steps.

The starting material is obtained as follows:

Preparation of bis(2-chloro-1-chloromethyl)ethoxy]methane

A mixture of 500 g of 1,3-dichloropropanol ($M_r$=128.9), 64 g of paraformaldehyde ($M_r$=30.03, based on formaldehyde) and 4.8 g of p-toluenesulfonic acid ($M_r$= 172.2) is reacted for 2 hours at 90° C. The water of reaction is subsequently removed by distillation. The reaction mixture is distilled under reduced pressure (c. 3 mbar), affording 374 g of c. 99% pure bis(2-chloro-1-chloromethyl) ethoxymethane (yield: 65% of theory). The reaction proceeds virtually without the formation of by-products. Unreacted 1,3-dichloropropanol can reused in the reaction, as can also the 1,3-dichloropropanol obtained as by-product in the above described reaction for the preparation of 1,3-dichloro-2-chloromethoxypropane.

The net reaction (both steps) thus makes it possible to obtain a high yield. The final reaction results in the formation of only an extremely minor amount of toxic bis (chloromethyl) ether and in a high purity of the product.

COMPARISON EXAMPLE (Analogous Procedure to that Described in U.S. Pat. No. 4,568,700)

With stirring, 37 g of hydrogen chloride are added to 129 g of 1,3-dichloropropanol and 30 g of paraformaldehyde at 22° C. over 5 hours. The net result is as follows:

| resultant compound | amount |
| --- | --- |
| 1,3-dichloro-2-chloromethoxypropane (product) | 115 g |
| bis(2-chloro-1-chloromethyl)ethoxymethane | 25.5 g |
| 1,3-dichloropropanol (educt) | 23 g |
| bis(chloromethyl) ether (toxic by-product) | 3.2 g |
| unknown by-products | 10 g |

The reaction mixture is distilled under reduced pressure (c. 20 mbar), affording only c. 97% pure 1,3-dichloro-2-chloromethoxypropane; yield 56% of theory.

EXAMPLE 2

Preparation of 1-chloromethoxy-2-methoxyethane 200 g of bis(2-methoxyethoxy)methane (1.218 mol; $M_r$=164.21) and 1 g of dimethyl formamide ($M_r$=73.10) are warmed to c. 45° C. With stirring, 147.8 g of thionyl chloride (1.242 mol; $M_r$=118.97) are added dropwise over 2 hours. Stirring is continued for 2 hours at 85° C. In the course of the reaction, altogether 74 g of sulfur dioxide evolve. The composition of the reaction mixture is determined in an aliquot of the mixture. The net result is as follows:

| resultant compound | amount |
| --- | --- |
| 1-chloromethoxy-2-methoxyethane (product; $M_r$ = 124.57) | 144 g |
| 2-methoxyethyl chloride (useful by-product, $M_r$ = 94.54) | 109.4 g |
| bis(2-methoxyethoxy)methane | 10 g |
| bis(chloromethyl) ether | 127 mg |

The reaction proceeds essentially in accordance with the following formula:

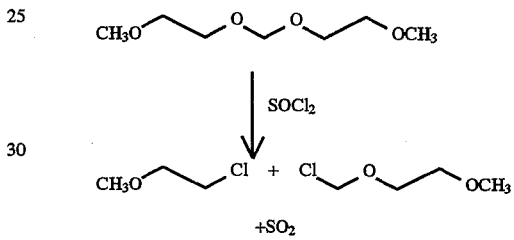

+SO$_2$

The reaction mixture is distilled under reduced pressure (c. 20 mbar), affording c. 99% pure 1-chloromethoxy-2-methoxyethane in a yield of 95% of theory.

The dimethyl formamide can be reused after the reaction for the same purpose, in which case it is advantageous to add an amount of flesh dimethyl formamide, or for other purposes.

The starting material can be prepared as follows:

Preparation of bis(2-methoxyethoxy)methane 1045 g of 2-methoxyethanol ($M_r$=76,1), 194 g of paraformaldehyde ($M_r$=30.03 based on formaldehyde) and 16 g of p-toluenesulfonic acid ($M_r$=172.2) are reacted for 2 hours at 90° C. The water of reaction is then removed by distillation. The reaction mixture is distilled under reduced pressure (c. 20 mbar), affording 758 g of bis(2-methoxyethoxy)methane ($M_r$=164.21) in c. 99% purity, yield: 67% of theory. The remainder (33%) consists almost completely of the educt, which can be recycled, so that total yields of over 97% result.

It is found that an extremely low amount of toxic bis-chloromethyl ether is formed in the overall process and that a product of high purity is obtained. The synthetically useful 2-methoxyethyl chloride is obtained as by-product.

COMPARISON EXAMPLE A (Analogous Procedure to that Described in U.S. Pat. No. 4,568,700; cf. also E. J. Corey et al., Tetrahedron Lett. 11,809–812 (1976))

With stirring, 72 g of hydrogen chloride are added to 152 g of 2-methoxyethanol and 66 g of paraformaldehyde at 22°

C. over 2 hours. The composition of the reaction mixture is determined in an aliquot of the mixture. The net result is as follows: (excluding water and water-soluble matter):

| resultant compound | amount |
|---|---|
| 1-chloromethoxy-2-methoxyethane (product) | 211.7 g |
| bis(2-methoxyethoxy)methane | 32.8 g |
| 2-methoxyethanol | 7.5 g |
| bis(chloromethyl) ether | 12.6 g |

The reaction mixture is diluted with 900 ml of pentane and dried over 100 g of magnesium sulfate. The mixture is distilled under reduced pressure (c. 20 mbar), affording c. 95% pure 1-chloromethoxy-2-methoxyethane; yield: 80% of theory.

COMPARISON EXAMPLE B (without dimethyl formamide)

200 g of bis(2-methoxyethoxy)methane (1.218 mol; $M_r$=164.21) are warmed to c. 45° C. With stirring, 147.8 g of thionyl chlorid (1.242 mol; $M_r$=118.97) are added dropwise over 2 hours. Stirring is continued for 2 hours at 85° C. In the course of the reaction, altogether 13 g of sulfur dioxide evolve. The composition of the reaction mixture is determined in an aliquot of the mixture. The net result is as follows:

| resultant compound | amount |
|---|---|
| 1-chloromethoxy-2-methoxyethane (product; $M_r$ = 124,57) | 121 g |
| 2-methoxyethyl chloride | 17 g |
| bis(2-methoxyethoxy)methane | 7 g |
| various by-products | 180 g |
| bis(chloromethyl) ether (toxic by-product) | 130 mg |

Separation of the reaction mixture by distillation can be effected only with great difficulty. Distillation under reduced pressure (c. 20 mbar) affords 165 mg of highly impure 1-chloromethoxy-2-methoxyethane (64% purity) yield: 70%.

EXAMPLE 3

Preparation of 1,3-dichloro-2-chloromethoxypropane 500 g of 1,3-dichloropropanol ($M_r$=128.9), 64 g of paraformaldehyde ($M_r$=30.03) and 4.8 g of p-toluenesulfonic acid ($M_r$=172.2) are reacted for 2 hours at 90° C. The water of reaction is then distilled from the reaction mixture. Unreacted 1,3-dichloropropanol is removed by distillation under reduced pressure (c. 20 mbar) (the starting material can be reused—c. 1 or less percent of 1,3-dichloropropanol in the residual reaction mixture obtained after distillation can remain in the batch and has a positive influence on the subsequent reaction). The reaction mixture is cooled to 60° C. and is treated with 4.8 g of dimethyl formamid ($M_r$=73.10).

With stirring, 177 g of thionyl chloride ($M_r$=118.978) are added dropwise over 2 hours. The reaction mixture is stirred for 3 hours at 110° C. In the course of the reaction, a total of 76 g of sulfur dioxide evolves. The composition of the reaction mixture is determined in an aliquot of the mixture. The net result is as follows:

| resultant compound | amount |
|---|---|
| 1,3-dichloro-2-chloromethoxypropane (product) | 209 g |
| 1,2,3-trichloropropane (by-product, $M_r$ = 147.43) | 173.8 g |
| bis[(2-chloro-1-chloromethyl)ethoxy]-methane (educt) | 6.4 g |
| bis(chloromethyl) ether | 3 mg |

The reaction mixture is distilled under reduced pressure (c. 10 mbar), affording 182 g of 1,3-dichloro-2-chloromethoxypropane in c. 99% purity ($M_r$=177.46).

COMPARISON EXAMPLE (without dimethyl formamide)

500 g of 1,3-dichloropropanol ($M_r$=128.9), 64 g of paraformaldehyde ($M_r$=30.03) and 4.8 g of p-toluenesulfonic acid ($M_r$=172.2) are reacted for 2 hours at 90° C. The water of reaction is then distilled from the reaction mixture. Unreacted 1,3-dichloropropanol is removed by distillation under reduced pressure (c. 20 mbar). The reaction mixture is cooled to 60° C.

With stirring, 177 g of thionyl chloride ($M_r$=118.978) are added dropwise over 2 hours, and the reaction mixture is stirred for 3 hours at 110° C. In the course of the reaction, a total of 3 g of sulfur dioxide evolves. The composition of the reaction mixture is determined in an aliquot of the mixture. The net result is as follows:

| resultant compound | amount |
|---|---|
| 1,3-dichloro-2-chloromethoxypropane (product) | 187 g |
| bis[(2-chloro-1-chloromethyl)ethoxy]-methane (educt) | 24 g |
| further by-products | 240 g |
| bis(chloromethyl) ether | 3 mg |

Separation of the reaction mixture by distillation can be effected only with great difficulty. Distillation under reduced pressure (c. 10 mbar) affords highly impure 1-chloromethoxy-2-methoxyethane (76% purity).

What is claimed is:

1. A process for the preparation of a compound of formula I

wherein

R is mono- or disubstituted $C_2$–$C_7$alkyl, the substituents being selected from halogen and lower alkoxy, with the proviso that said substituents are not present at the carbon atom of the lower alkyl radical R linking the group R to the remainder of the molecule of formula I;

$R_1$ is hydrogen, lower alkyl, phenyl or phenyl-lower alkyl; and

X is chloro or bromo;

which comprises reacting an acetal of formula II,

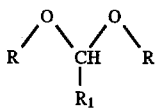
(II)

wherein

R and $R_1$ are as defined above, with at least one compound of formula $R_2$—X, wherein $R_2$ is
- (i) hydrogen, in which case working up is effected by distillation directly from the resulting reaction mixture, or
- (ii) X—SO, in which case the reaction mixture must contain a catalytically effective amount of N,N-di-lower alkyl-lower alkanoylamide(s)

and wherein

X is as defined with respect to the compound of formula I.

2. A process according to claim 1 for the preparation of a compound of formula I, wherein R is $C_2$–$C_7$alkyl of more than 2 carbon atoms which is mono- or disubstituted by halogen or by $C_1$–$C_4$alkoxy, with the proviso that said substituents are not present at the carbon atom of the lower alkyl radical R linking the group R to the remainder of the molecule of formula I;

$R_1$ is hydrogen; and

X is chloro or bromo, which process comprises using the appropriately substituted starting materials.

3. A process according to claim 1 for the preparation of a compound of formula I, wherein R is 1,3-dihalo-2-$C_3$–$C_4$alkyl, or 2-($C_1$–$C_4$alkoxy)ethyl;

$R_1$ is hydrogen; and

X is chloro or bromo, which comprises using the appropriately substituted starting materials.

4. A process according to claim 1 for the preparation of 1,3-dichloro-2-chloromethoxypropane of formula I, which comprises using the appropriately substituted starting materials.

5. A process according to claim 1 for the preparation of 1-chloromethoxy-2-methoxyethane of formula I, which comprises using the appropriately substituted starting materials.

6. A process according to claim 3, which comprises carrying out the reaction in the absence of further solvents, using a 1.01- to 10-fold excess of the compound of formula I over the compound of formula II, carrying out the reaction in the temperature range from 0° C. to 150° C., under atmospheric pressure or superatmospheric pressure, and subsequently working up the reaction mixture by distillation.

7. A process according to claim 1, which comprises heating a mixture of an acetal of formula II to about 50°–70° C., introducing a c. 1.05- to 8-fold excess of the corresponding hydrogen chloride or hydrogen bromide ($R_2$—X) in gaseous form over about 2 to 10 hours; or adding dropwise a 1.01- to 3-fold excess of thionyl chloride or thionyl bromide (as $R_2$—X) over 1 to 5 hours, in which case a pretreatment with a minor amount of hydrogen chloride or hydrogen bromide can be first effected at a temperature in the range from 10° to 115° C., allowing the reaction to proceed under stirring for further 0 to 5 hours; and thereafter working up the resultant reaction mixture by distillation under reduced pressure.

8. A process according to claim 1 for the preparation of a compound of formula I, wherein R, $R_1$ and X are as defined in claim 1, which comprises reacting an alcohol of formula III

R—OH (III)

wherein R is as defined for compound of formula I, with an appropriate aldehyde of formula IV $R_1$—CHO (IV)

wherein $R_1$ is as defined for the compound of formula I, or a reactive derivative thereof, to an acetal of formula II

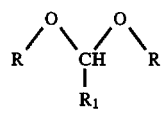
(II)

wherein R and $R_1$ have the above meanings, solely with removal of the water of reaction by distillation and of any unreacted starting material of formula III, but without subsequent isolation of the acetal of formula II in pure form, and thereafter further reacting the resultant reaction mixture direct with $X_2SO$, wherein X is as defined for compound of formula I, with the proviso that a catalytically effective amount of N,N-di-lower alkyl-lower alkanoylamide(s) must be present.

9. A process according to claim 8 for the preparation of 1,3-dichloro-2-chloromethoxypropane of formula I, which comprises reacting paraformaldehyde with a molar excess of 1,3-dichloropropan-2-ol in the presence of an aliphatic or aromatic sulfonic acid in the presence or in the absence of solvents, at elevated temperature, to bis[(2-chloro-1-chloromethyl)ethoxy]methane of formula II, removing the water of reaction by distillation, if necessary distilling off unreacted 1,3-dichloropropan-2-ol under reduced pressure, and reacting the resulting mixture by adding a N,N-di-lower alkyl-lower alkanoylamide and a compound of formula $R_2$—X, wherein $R_2$ is X—SO and X is as defined in claim 1, in the temperature range from 0° to 150° C., to give the final product which is obtained in pure form by working up.

10. A process according to claim 8 for the preparation of 1,3-dichloro-2-chloromethoxypropane of formula I, which comprises reacting paraformaldehyde, with a 1.5- to 10-fold molar excess of 1,3-dichloropropan-2-ol in the presence of p-toluenesulfonic acid, in the temperature range from c. 60° to 100° C., to bis[(2-chloro-1-chloromethyl)ethoxy]methane of formula II, removing the water of reaction by distillation, if necessary distilling off unreacted 1,3-dichloropropan-2-ol under reduced pressure; and reacting the resulting mixture by adding N,N-dimethylformamide in the 0.0001 to 0.1-fold molar excess over the bis[(2-chloro-1-chloromethyl)ethoxy] methane of formula II and dropwise thionyl chloride in the 1.01- to 10-fold excess over the compound of formula II, in the temperature range from 15° to 115° C., to give the final product which is obtained in pure form by distillation.

* * * * *